United States Patent [19]

Carson et al.

[11] 4,166,854
[45] Sep. 4, 1979

[54] SUBSTITUTED 1-PYRIDINYLOXY-1-(IMIDAZOLYL)-2-BUTANONE COMPOUNDS AND THEIR USE AS FUNGICIDES

[75] Inventors: Chrislyn M. Carson; Robert J. Ehr, both of Pittsburg; Richard B. Rogers, Concord, all of Calif.

[73] Assignee: The Dow Chemical Company, Midland, Mich.

[21] Appl. No.: 956,957

[22] Filed: Nov. 2, 1978

[51] Int. Cl.$^2$ .................... C07D 401/06; A61K 31/44
[52] U.S. Cl. .................................... 424/263; 546/276
[58] Field of Search ........................ 546/276; 424/263

[56] References Cited
FOREIGN PATENT DOCUMENTS 2325156 12/1974 Fed. Rep. of Germany ........... 548/339

Primary Examiner—Alan L. Rotman
Attorney, Agent, or Firm—S. Preston Jones; Ronald G. Brookens

[57] ABSTRACT

Substituted 1-pyridinyloxy-1-(triazolyl or imidazolyl)-2-butanone compounds which correspond to the formula:

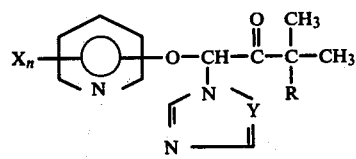

wherein each X independently represents halogen, methyl, trichloromethyl, trifluoromethyl, or cyano; n represents an integer of 0 to 3; Y represents —N or —CH; and R represents methyl, methoxy, or ethoxy are prepared. These compounds have been found to exhibit a high degree of fungicidal activity, and compositions containing said compounds are so employed.

36 Claims, No Drawings

SUBSTITUTED 1-PYRIDINYLOXY-1-(IMIDAZOLYL)-2-BUTANONE COMPOUNDS AND THEIR USE AS FUNGICIDES

DESCRIPTION OF PRIOR ART

1-Phenoxy-1-(1,2,4-triazol-1-yl)-2-alkanone compounds and derivatives having fungicidal activity are disclosed in German Offen. No. 2,201,063 (Chemical Abstracts 79, 105257y (1973)) and German Offen. No. 2,247,186 (Chemical Abstracts 80, 146129k (1974)).

SUMMARY OF THE INVENTION

The present invention is directed to novel substituted 1-pyridinyloxy-1-(triazolyl or imidazolyl)-2-butanone compounds, to compositions containing said active compounds, and to the use of such compositions for control of fungi that attack plants. The compounds of the present invention correspond to the formula

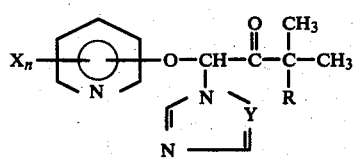

wherein each X independently represents halogen, methyl, trichloromethyl, trifluoromethyl, or cyano; n represents an integer of 0 to 3; Y represents —N or —CH; and R represents methyl, methoxy, or ethoxy.

In the present specification and claims, the term "halogen" is employed to designate chloro, fluoro, or bromo.

The compounds of the invention are solids at ambient temperatures and are of low mammalian toxicity. The compounds are substantially insoluble in water and usually are moderately to highly soluble in common organic solvents.

The compounds of the present invention can be prepared by the reaction of substantially equimolar amounts of 1H-1,2,4-triazole or imidazole with an appropriate 1-halo-1-pyridinyloxy-1,1-dimethyl-2-butanone compound corresponding to the formula

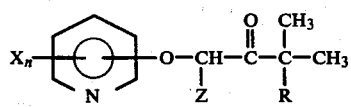

wherein X, n, and R are as defined hereinabove, and Z is bromo or chloro. The reaction is carried out in presence of a solvent and a hydrogen halide acceptor. Preferably, the reaction is carried out at a temperature within the range of from −10° to 110° C., most preferably from 0° to 35° C.

Suitable solvents useful in carrying out the reaction include acetone, acetonitrile, halogenated hydrocarbon solvents such as methylene chloride, and hydrocarbon solvents such as hexane, benzene, or toluene. Suitable hydrogen halide acceptors useful in carrying out the reaction include conventional bases, such as potassium or sodium carbonate, triethylamine and 1,5-diaza(5.4.-0)undec-5-ene as is well known to those skilled in the art.

The product of the reaction can be purified as desired using well known procedures, such as recrystallization from a solvent.

DESCRIPTION OF SOME PREFERRED EMBODIMENTS

The following examples illustrate the present invention and the manner by which it can be practiced, but as such, should not be construed as limitations on the overall scope of the same.

PREPARATION OF INTERMEDIATES

EXAMPLE I

1-Bromo-1-(5-chloro-2-pyridinyloxy)-3,3-dimethyl-2-butanone

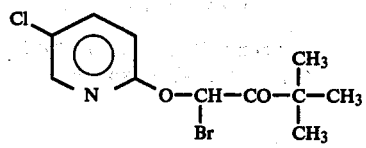

A mixture of 12.96 grams (g) (0.1 mole) of 5-chloro-2-hydroxypyridine, 17.9 g (0.1 mole) of 1-bromo-3,3-dimethyl-2-butanone, and 15 g (0.054 mole) of silver carbonate in hexane was stirred and heated at reflux temperature for 48 hours. The reaction mixture was filtered, and the solvent removed by evaporation. The residue was dissolved in methylene chloride and filtered through silica gel. Evaporation of the solvent gave 10.5 g (46 percent (%) yield) of 1-(5-chloro-2-pyridinyloxy)-3,3-dimethyl-2-butanone. A sample recrystallized from pentane had a melting point of 68°–69.5° C.

A mixture of 10.5 g (0.046 mole) 1-(5-chloro-2-pyridinyloxy)-3,3-dimethyl-2-butanone, prepared above, and 8.37 g (0.047 mole) N-bromosuccinimide (NBS) in 300 ml. carbon tetrachloride, with stirring, was irradiated and heated with a sunlamp until all of the NBS was consumed (about 45 min.). The reaction mixture was cooled, filtered, and the filtrate washed with aqueous sodium bisulfite and dried. After removal of the solvent, there was obtained a quantitative yield of 1-bromo-1-(5-chloro-2-pyridinyloxy)-3,3-dimethyl-2-butanone, a light yellow oil.

EXAMPLE II

1-Bromo-1-(6-chloro-2-pyridinyloxy)-3,3-dimethyl-2-butanone

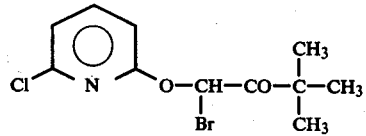

To a stirred mixture of 400 g (3.09 moles) of 2-hydroxy-6-chloropyridine and 450 g (3.26 moles) potassium carbonate in 3000 ml acetonitrile was added 551 g (3.08 moles) 1-bromo-3,3-dimethyl-2-butanone. The reaction mixture was stirred at 45°–50° C. for 1.5 hours and then filtered. The solids were washed several times with acetonitrile, the filtrate dried (MgSO$_4$) and the solvent evaporated. Crystallization of the residue from pentane gave 610 g (87% yield) of 1-(6-chloro-2-pyridinyloxy)-3,3-dimethyl-2-butanone. A second recrystallization from pentane gave product melting at 43°-44.5° C.

A stirred solution of 227.68 g (1.0 mole) of 1-(6-chloro-2-pyridinyloxy)-3,3-dimethyl-2-butanone, prepared above, in 1000 ml dioxane was heated to 65° C. The heat source was removed and 175.8 g (1.1 mole) bromine added dropwise. After the addition of the bromine, the solution was stirred for 10 minutes and then poured into 3 liters ice water containing 25 g sodium bisulfite. The mixture was made slightly basic with 50% NaOH and twice extracted with 500-ml portions of pentane. The pentane extracts were washed with 1000 ml of 5% NaOH and dried, giving 259 g (84% yield) of 1-bromo-1-(6-chloro-2-pyridinyloxy)-3,3-dimethyl-2-butanone. Crystallization from pentane gave a white solid melting at 50°-52° C.

EXAMPLE III 1-(6-Chloro-2-pyridinyloxy)-3,3-dimethyl-1-(1,2,4-triazol-1-yl)-2-butanone

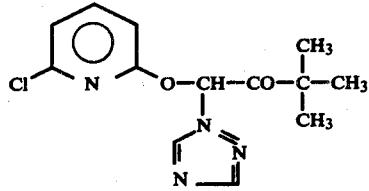

A solution of 259 g (0.845 mole) of 1-bromo-1-(6-chloro-2-pyridinyloxy)-3,3-dimethyl-2-butanone in 300 ml acetone was added dropwise to a stirred solution of 58.4 g (0.845 mole) 1H-1,2,4-triazole and 124.4 g (0.9 mole) potassium carbonate in 500 ml acetone. The reaction mixture was maintained at a temperature below 35° C. After the addition was complete, the mixture was stirred for 30 minutes and then filtered. The solid product was washed with acetone and dried. Crystallization from 800 ml methanol and 200 ml water gave 170 g (69% yield) of 1-(6-chloro-2-pyridinyloxy)-3,3-dimethyl-1-(1,2,4-thiazol-1-yl)-2-butanone melting at 106°-107.5° C.

| Elemental analysis | C | H | N |
|---|---|---|---|
| Theory | 52.97 | 5.13 | 19.01 |
| Found | 52.90 | 5.22 | 18.83 |

EXAMPLE IV 1-(6-Fluoro-2-pyridinyloxy)-3,3-dimethyl-1-(imidazol-1-yl)-2-butanone

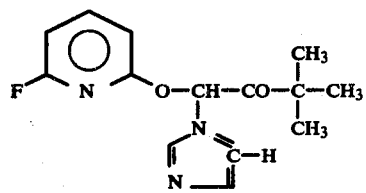

To a stirred solution of 14.5 g (0.05 mole) of 1-bromo-1-(6-fluoro-2-pyridinyloxy)-3,3-dimethyl-2-butanone in 75 ml acetone cooled to −10° C. was added 3.4 g (0.05 mole) imidazole. Then, 7.61 g (0.05 mole) of 1,5-diaza(5.4.0)undec-5-ene was added dropwise. After the addition was complete, the mixture was stirred for 30 minutes at 0° C. and the solvent evaporated. Water was added to the residue and the mixture extracted with diethyl ether. The ether extract was dried using magnesium sulfate and the solvent evaporated. Chromatography on silica gel (8:2 hexane:acetone) gave 6.3 g (55% yield) of 1-(6-fluoro-2-pyridinyloxy)-3,3-dimethyl-1-(imidazol-1-yl)-2-butanone. Recrystallization from hexane gave product melting at 90°-93° C.

| Elemental analysis: | C | H | N |
|---|---|---|---|
| Theory | 60.64 | 5.82 | 15.15 |
| Found | 60.44 | 5.84 | 15.07 |

Using similar procedures, additional compounds of the present invention listed in Table 1 were prepared.

TABLE 1

| Example | Oxy Position | Xn | Y | R | Melting Point ° C. | | Elemental Analysis | | |
|---|---|---|---|---|---|---|---|---|---|
| | | | | | | | C | H | N |
| V | 2 | 5-Cl | N | CH₃ | 97.9 | | | | |
| VI | 2 | 3,5-Cl | N | CH₃ | 98-100 | T* | 47.43 | 4.29 | 17.02 |
| | | | | | | F | 47.60 | 4.43 | 16.88 |
| VII | 2 | 3,5-Cl; 6-F | N | CH₃ | 105-109 | T | 44.97 | 3.77 | 16.14 |
| | | | | | | F | 44.86 | 3.74 | 15.89 |
| VIII | 2 | 6-F | N | CH₃ | 108-110 | T | 56.10 | 5.43 | 20.13 |
| | | | | | | F | 55.86 | 5.45 | 19.94 |
| IX | 2 | 3,5,6-F | N | CH₃ | 104-105.5 | T | 49.68 | 4.17 | 17.83 |
| | | | | | | F | 49.53 | 4.17 | 17.65 |
| X | 2 | 3,5,6-Cl | N | CH₃ | 127.5-129.5 | T | 42.94 | 3.60 | 15.41 |
| | | | | | | F | 42.87 | 3.62 | 15.30 |
| XI | 2 | 3,6-Cl | N | CH₃ | 146.5-148.5 | T | 47.43 | 4.29 | 17.02 |
| | | | | | | F | 47.19 | 4.33 | 16.59 |
| XII | 2 | 5,6-Cl | N | CH₃ | 130-133 | T | 47.43 | 4.29 | 17.02 |
| | | | | | | F | 47.51 | 4.29 | 16.87 |
| XIII | 2 | | N | CH₃ | 80-83 | | | | |
| XIV | 2 | 5-CN | N | CH₃ | 149-150.5 | T | 58.93 | 5.30 | 24.55 |

TABLE 1-continued

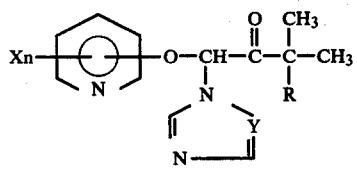

| Example | Oxy Position | Xn | Y | R | Melting Point °C. | | Elemental Analysis | | |
|---|---|---|---|---|---|---|---|---|---|
| | | | | | | | C | H | N |
| | | | | | | F | 58.72 | 5.44 | 24.31 |
| XV | 2 | 6-Cl 4-CCl$_3$ | N | CH$_3$ | 135–137.5 | T | 40.80 | 3.42 | 13.60 |
| | | | | | | F | 40.65 | 3.53 | 13.29 |
| XVI | 2 | 5-CF$_3$ | N | CH$_3$ | 88–90 | T | 51.22 | 4.61 | 17.07 |
| | | | | | | F | 51.34 | 4.68 | 16.86 |
| XVII | 2 | 6-CH$_3$ | N | CH$_3$ | 123–124.5 | T | 61.30 | 6.61 | 20.43 |
| | | | | | | F | 61.18 | 6.56 | 20.10 |
| XVIII | 2 | 6-Cl | N | OCH$_3$ | 105–106 | T | 50.24 | 4.87 | 18.03 |
| | | | | | | F | 49.83 | 4.80 | 17.76 |
| XIX | 2 | 6-Cl | N | OC$_2$H$_5$ | 114–120 | | | | |
| XX | 2 | 5-CN | CH | CH$_3$ | 176–178 | T | 63.36 | 5.67 | 19.71 |
| | | | | | | F | 63.51 | 5.66 | 19.83 |
| XXI | 4 | 2,6-Cl | N | CH$_3$ | 104–106 | | | | |
| XXII | 4 | 2,6-CH3 | N | CH$_3$ | oil | | | | |
| XXIII | 2 | 4,6-Cl | N | CH$_3$ | 115–117 | T | 47.43 | 4.29 | |
| | | | | | | F | 47.68 | 4.35 | |
| XXIV | 3 | 2,6-Br | N | CH$_3$ | | | | | |

*T = theory; F = found.

In accordance with this invention, it has been found that the compounds of the present invention are adapted to be employed as fungicidal agents for the control of a wide variety of fungal organisms. The compounds are particularly adapted to be employed for the control of fungal organisms found on plants, such as, for example, barley powdery mildew (*Erysiphe graminis hordeii*), grape downy mildew (*Plasmopara viticola*), wheat rusts (*Puccinia sp*), verticillium wilt (*Verticillium albo-atrum*), apple powdery mildew (*Podosphaera leucotricha*), tobacco black root rot (*Thielaviopsis basicola*), apple scab (*Venturia inaequalis*) and other such organisms. In such uses, the compounds are usually applied to the aerial portions of plants. The compounds also can be applied in dormant applications to the woody surfaces of plants or to orchard floor surfaces for the control of overwintering spores of many fungi. In addition, the compounds can be applied to seeds to protect the foliage of the growing plant from attack of fungal organisms such as those causing rust or mildew. Furthermore, the compounds can be applied or distributed in soil for control of fungal organisms that attack seeds or plant roots, particularly those organisms that cause root rot or wilt.

In further operations, the compounds can be included in inks, adhesives, soaps, cutting oils, polymeric materials, oil paints, or latex paints to prevent mold, mildew, or degradation of such materials resulting from microbial attack. Additionally, the compounds can be distributed in textile or cellulosic materials, or they can be employed in the impregnation of wood or lumber to protect such products from fungal organism which cause rot, mold, mildew, or decay.

It is an advantage of the present invention that compositions containing the compounds can be applied to vegetation or soil in amounts required for effective control without significant injury to plants. A further advantage is that the compounds exhibit very low mammalian toxicity at the rates employed for control of fungal organisms. Another advantage is that a single application of the compounds can provide a residual, extended control of fungi for a period of several months. Also, the compounds can be effective in eliminating established fungal infestation. Furthermore, the compounds have been found to be translocated in plants and thus can provide a systemic protection against fungi that attack plants.

Generally in the actual practice of the method of the present invetion, a plant protecting amount of the toxicant compounds can be applied to the plant by such convenient procedures as soil injection, drenching with an aqueous composition, seed treatment, topical spraying, furrow spraying, or other techniques known to those skilled in the art.

The exact dosage of the active toxicant employed can be varied depending upon the specific plant, disease to be controlled, hardiness of the plant, and the mode of application. Generally, the active ingredient should be present in an amount equivalent to from about 50 micrograms to about 125 milligrams or more per plant. Translating this into conventional application rates, this amount is equivalent to from about 0.001 pound to about 2 pounds or more of the active ingredient on a per acre basis (0.0013–2.24 kilogram per hectare), as chemical available to the plant.

Larger amounts of the active ingredient advantageously may be applied when treatments are employed which distribute the material throughout the soil. For example, when the active ingredient is applied as an at-plant row treatment or as an early season post-plant side dress treatment, those amounts of chemical not proximal to plant roots are essentially unavailable to the plant and therefore not effective as set forth hereinabove. In such practices, amounts of the active ingredient need to be increased to rates as high as about 10 pounds per acre (11.2 kg/hectare) to assure the requisite effective quantity of active ingredient is made available to the plants.

The present invention can be carried out by employing the compounds directly, either singly or in combination. However, the present invention also embraces the employment of liquids, dusts, wettable powders, granules, or encapsulated compositions containing at least one of said compounds as active ingredient. In such usage, the compound or compounds can be modified with one or more of a plurality of additaments or adjuvants including inert solvents, inert liquid carriers, wetting agents and/or surface active dispersing agents and coarsely or finely divided inert solids. The augmented compositions are also adapted to be employed as concentrates and subsequently diluted with additional inert carrier to produce other compositions in the form of dusts, sprays, granules, washes, or drenches. In compositions where the adjuvant is a coarsely or finely divided solid, a surface active agent, or the combination of a surface active agent and a liquid additament, the adjuvant cooperates with the active component so as to facilitate the invention. Whether the composition is employed in liquid, wettable powder, dust, granule, or encapsulated form, the active compound will normally be present in an amount of from about 2 to 98 percent by weight of the total composition.

In the preparation of dust, or wettable powder compositions, the toxicant products can be compounded with any of the finely divided solids, such as pyrophyllite, talc, chalk, gypsum, fuller's earth, bentonite, attapulgite, starch, casein, gluten, or the like. In such operations, the finely divided carrier is ground or mixed with the toxicant or wet with a solution of the toxicant in a volatile organic solvent. Also, such compositions when employed as concentrates can be dispersed in water, with or without the aid of dispersing agents to form spray mixtures.

Granular formulations are usually prepared by impregnating a solution of the toxicant in a volatile organic solvent onto a bed of coarsely divided attapulgite, bentonite, diatomite, or the like.

Similarly, the toxicant products can be compounded with a suitable water-immiscible inert organic liquid and a surface active dispersing agent to produce an emulsifiable concentrate which can be further diluted with water and oil to form spray mixtures in the form of oil-in-water emulsions. In such compositions, the carrier comprises an aqueous emulsion, i.e., a mixture of inert water-immiscible solvent, emulsifying agent, and water. Preferred dispersing agents which can be employed in these compositions, are oil-soluble materials including non-ionic emulsifiers such as the condensation products of alkylene oxides with the inorganic acids, polyoxyethylene derivatives or sorbitan esters, complex ether alcohols, and the like. Also, oil-soluble ionic emulsifying agents such as mahogany soaps can be used. Suitable inert organic liquids which can be employed in the compositions include petroleum oils and distillates, toluene, liquid halohydrocarbons, and synthetic organic oils. The surface-active dispersing agents are usually employed in liquid compositions and in the amount of from 0.1 to 20 percent by weight of the combined weight of the dispersing agent and active compound.

In addition, other liquid compositions containing the desired amount of effective agent can be prepared by dissolving the toxicant in an inert organic liquid such as acetone, methylene chloride, chlorobenzene, or petroleum distillates. The preferred inert organic solvent carriers are those which are adapted to accomplish the penetration and impregnation of the plant and particularly soil with the toxicant compounds and are of such volatility as to leave little permanent residue thereon. Particularly desirable carriers are the petroleum distillates boiling almost entirely under 400° F. (204° C.) at atmospheric pressure and having a flash point above 80° C. The proportion of the compounds of this invention employed in a suitable solvent may vary from about 2 to about 50 percent or higher.

A preferred liquid composition includes the use of the active compound or compounds in combination with surface active dispersant agents only. In such compositions, it is preferred to use ionic and non-ionic blends of such dispersant agents in combination with one or more of the active materials. A particular advantage of such a formulation is that phytotoxicity associated with certain inert solvents, such as xylene, methylene chloride, or like materials can be avoided. Generally, the use of such formulations will result in compositions containing 75 percent or more of the active component.

Owing to the excellent suspensibility of the above formulation in water, it is convenient and often preferred to prepare and use aqueous concentrates as stock solutions themselves. In such practices, minor agitation results in a practical, stable formulation very adaptable for use in its concentrate form to treat soil in sprays or drenches. Additionally, if desired, the concentrates can be easily diluted with additional water for use as foliar spray treatments, soil drench treatments, and the like.

Water miscible organic solvents such as lower alcohols or propylene glycol can be added to depress the freezing point and further cooperate with the above system in that they are essentially non-phytotoxic.

The following examples further illustrate the present invention, but, as such, are not to be construed as limiting in scope.

EXAMPLE XXV

The compound of Example III, -(5-chloro-2-pyridinyloxy)-3,3-dimethyl-1(1H-1,2,4-triazol-1-yl)-2-butanone, was dissolved in acetone. Aliquots of the solution were diluted with water to provide dispersions containing 1.6, 6.2, and 25 parts per million by weight of the test compound (PPM). Tobacco plant seedlings were transplanted into 2-inch (5 cm) diameter pots containing soil infested with tobacco black root rot (*Thielaviopsis basicola*). Immediately after transplanting, the pots were drenched with 40 ml of solution, two pots per dilution. Control pots were drenched with acetone solution containing no test compound. The pots were maintained at a temperature of 60° F. (15.5° C.) and watered daily. The test was evaluated by estimating the percentage of root system that was injured, the evaluation being made when roots of plants in the control pots showed 98 percent injury. The plants treated with solution containing 1.6 ppm test compound showed 15 percent root injury, and plants treated with solutions containing 6.2 and 25 ppm test compound showed no root injury.

EXAMPLE XXVI

In two separate series of tests, the foliage of apple tree seedlings was sprayed to run off with solutions of compounds of the invention prepared as described above in Example XXI. Four days after the treatment, the plants were inoculated with spores of *Venturia inaequalis*. One week after the inoculation, the percent control of apple scab disease was determined. The identity of test compound, concentration thereof, and the results are set forth in Table II.

TABLE II

| Compound of Example No. | Concentration of Test Compound ppm | Percent Control of Venturia inaequalis at indicated Concentrations | |
|---|---|---|---|
| | | First Series | Second Series |
| III | 19 | 95 | 99 |
| | 75 | 99 | 100 |
| | 300 | 100 | 100 |
| V | 19 | 75 | 90 |
| | 75 | 99 | 100 |
| | 300 | 100 | 100 |
| VI | 19 | NT* | 97 |
| | 75 | NT | 99 |
| | 300 | NT | 100 |
| VII | 19 | 90 | NT |
| | 75 | 99 | NT |
| | 300 | 100 | NT |
| VIII | 19 | 0 | NT |
| | 75 | 95 | NT |
| | 300 | 100 | NT |
| IX | 19 | 100 | 95 |
| | 75 | 100 | 100 |
| | 300 | 100 | 100 |

*NT = not tested.

EXAMPLE XXVII

Three separate series of test were conducted by the procedure described in Example XXII, except the apple seedlings were inoculated with spores of *Podosphaera leucotricha*. The results are set forth in Table III.

TABLE III

| Compound of Example No. | Concentration of Test Compound ppm | Percent Control of Podosphaera leucotricha | | |
|---|---|---|---|---|
| | | First Series | Second Series | Third Series |
| III | 19 | 50 | 50 | 25 |
| | 75 | 93 | 93 | 83 |
| | 300 | 99 | 100 | 100 |
| V | 19 | 90 | 35 | 75 |
| | 75 | 97 | 97 | 99 |
| | 300 | 100 | 100 | 100 |
| VI | 19 | NT | NT | 35 |
| | 75 | NT | NT | 93 |
| | 300 | NT | NT | 100 |
| VII | 19 | NT | NT | 93 |
| | 75 | NT | NT | 98 |
| | 300 | NT | NT | 100 |
| VIII | 19 | 0 | NT | 0 |
| | 75 | 90 | NT | 90 |
| | 300 | 99 | NT | 100 |
| IX | 19 | 83 | 50 | 60 |
| | 75 | 99 | 95 | 99 |
| | 300 | 99 | 100 | 100 |
| XI | 19 | NT | NT | 25 |
| | 75 | NT | NT | 75 |
| | 300 | NT | NT | 100 |
| XII | 19 | NT | NT | 25 |
| | 75 | NT | NT | 98 |
| | 300 | NT | NT | 100 |
| XIV | 19 | 25 | NT | 0 |
| | 75 | 50 | NT | 35 |
| | 300 | 75 | NT | 99 |
| XVI | 19 | NT | NT | 0 |
| | 75 | NT | NT | 35 |
| | 300 | NT | NT | 99 |
| XVII | 19 | NT | NT | 0 |
| | 75 | NT | NT | 35 |
| | 300 | NT | NT | 97 |
| XVIII | 19 | NT | NT | 0 |
| | 75 | NT | NT | 0 |
| | 300 | NT | NT | 90 |

EXAMPLE XXVIII

This example demonstrates the systemic character of compounds of the invention. Aqueous compositions containing 0.4, 1.6, 6.2 and in some instances 25 ppm of test compound were prepared as described in Example XXI. The compositions were drenched onto soil in which apple plant seedlings were growing. One week later, the plant foliage was sprayed with a suspension of spores of apple powdery mildew (*Podosphaera leucotricha*). When disease symptoms on control plants developed, evaluation of percent control on plants in treated pots was made. The results are set forth in Table IV.

TABLE IV

| Compound of Example No. | Percent Control of Podosphaera leucotricha at indicated Concentration | | | |
|---|---|---|---|---|
| | 0.4 ppm | 1.6 ppm | 6.2 ppm | 25 ppm |
| III | 83 | 99 | 100 | 100 |
| IV | 0 | 0 | 25 | 83 |
| V | 97 | 99 | 100 | 100 |
| VI | 75 | 90 | 99 | 100 |
| VII | 0 | 25 | 99 | 99 |
| VIII | 97 | 99 | 99 | 100 |
| IX | 97 | 100 | 100 | 100 |
| XI | 25 | 97 | 99 | NT |
| XIII | 50 | 90 | 99 | 100 |
| XIV | 0 | 0 | 25 | 75 |
| XVI | 0 | 35 | 95 | 100 |
| XVII | 0 | 35 | 100 | NT |
| XVIII | 0 | 0 | 83 | NT |

What is claimed is:

1. A substituted 1-pyridinyloxy-1-(triazolyl or imidazolyl)-2-butanone compound corresponding to the formula

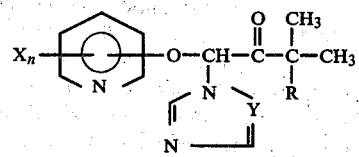

wherein X independently represents halogen, methyl, trichloromethyl, trifluoromethyl, or cyano; n represents an integer of 0 to 3; Y represents —N; and R represents methyl, methoxy, or ethoxy.

2. A compound as defined in claim 1 wherein X is chloro.

3. A compound as defined in claim 1 wherein Y is —N.

4. A compound as defined in claim 1 wherein R is methyl.

5. A compound as defined in claim 4 wherein X is chloro and Y is —N.

6. A compound as defined in claim 4 wherein X is fluoro and Y is N.

7. The compound as defined in claim 5 which is 1-(5-chloro-pyridinyloxy)-3,3-dimethyl-1-(1H-1,2,4-triazol-1-yl)-2-butanone.

8. The compound as defined in claim 5 which is 1-(6-chloro-2-pyridinyloxy)-3,3-dimethyl-1-(1H-1,2,4-triazol-1-yl)-2-butanone.

9. The compound as defined in claim 4 which is 1-(3,5-dichloro-6-fluoro-2-pyridinyloxy)-3,3-dimethyl-1-(1H-1,2,4-triazol-1-yl)-2-butanone.

10. The compound as defined in claim 6 which is 1-(3,5,6-trifluoro-2-pyridinyloxy)-3,3-dimethyl-1-(1H-1,2,4-triazol-1-yl)-2-butanone.

11. The compound as defined in claim 6 which is 1-(6-fluoro-2-pyridinyloxy)-3,3-dimethyl-1-(1H-1,2,4-triazol-1-yl)-2-butanone.

12. The compound as defined in claim 5 which is 1-(5,6-dichloro-2-pyridinyloxy)-3,3-dimethyl-1-(1H-1,2,4-triazol-1-yl)-2-butanone.

13. A fungicidal composition comprising as active ingredient a fungicidally effective amount of a substituted 1-pyridinyloxy-1-(triazolyl or imidazolyl)-2-butanone compound corresponding to the formula

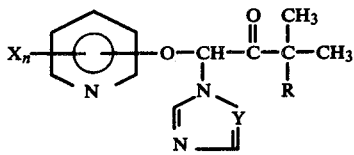

wherein X independently represents halogen, methyl, trichloromethyl, trifluoromethyl, or cyano; n represents an integer of 0 to 3; Y represents —N; and R represents methyl, methoxy, or ethoxy, in intimate admixture with an inert carrier therefor.

14. A composition as defined in claim 13 wherein X is chloro.

15. A composition as defined in claim 13 wherein Y is —N.

16. A composition as defined in claim 13 wherein R is methyl.

17. A composition as defined in claim 16 wherein X is chloro and Y is —N.

18. A composition as defined in claim 16 wherein X is fluoro and Y is —N.

19. The composition as defined in claim 17 wherein the compound is 1-(5-chloro-2-pyridinyloxy)-3,3-dimethyl-1-(1H-1,2,4-triazol-1-yl)-2-butanone.

20. The composition as defined in claim 17 wherein the compound is 1-(6-chloro-2-pyridinyloxy)-3,3-dimethyl-1-(1H-1,2,4-triazol-1-yl)-2-butanone.

21. The composition as defined in claim 16 wherein the compound is 1-(3,5-dichloro-6-fluoro-2-pyridinyloxy)-3,3-dimethyl-1-(1H-1,2,4-triazol-1-yl)-2-butanone.

22. The composition as defined in claim 18 wherein the compound is 1-(3,5,6-trifluoro-2-pyridinyloxy)-3,3-dimethyl-1-(1H-1,2,4-triazol-1-yl)-2-butanone.

23. The composition as defined in claim 18 wherein the compound is 1-(6-fluoro-2-pyridinyloxy)-3,3-dimethyl-1-(1H-1,2,4-triazol-1-yl)-2-butanone.

24. The composition as defined in claim 17 wherein the compound is 1-(5,6-dichloro-2-pyridinyloxy)-3,3-dimethyl-1-(1H-1,2,4-triazol-1-yl)-2-butanone.

25. A method for controlling fungi which attack plants which comprises applying to plants, plant parts, or soil a composition containing as the active ingredient, a fungicidally effective amount of a substituted 1-pyridinyloxy-1-(triazolyl or imidazolyl)-2-butanone compound corresponding to the formula

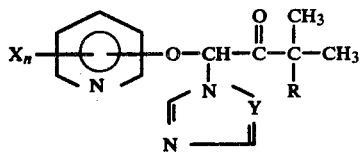

wherein X independently represents halogen, methyl, trichloromethyl, trifluoromethyl, or cyano; n represents an integer of 0 to 3; Y represents —N; and R represents methyl, methoxy, or ethoxy, in intimate admixture with an inert carrier therefor.

26. A method as defined in claim 25 wherein X is chloro.

27. A method as defined in claim 25 wherein Y is —N.

28. A method as defined in claim 25 wherein R is methyl.

29. A method as defined in claim 28 wherein X is chloro and Y is —N.

30. A method as defined in claim 28 wherein X is fluoro and Y is —N.

31. The method as defined in claim 29 wherein the active ingredient is 1-(5-chloro-2-pyridinyloxy)-3,3-dimethyl-1-(1H-1,2,4-triazol-1-yl)-2-butanone.

32. The method as defined in claim 29 wherein the active ingredient is 1-(6-chloro-2-pryidinyloxy)-3,3-dimethyl-1-(1H-1,2,4-triazol-1-yl)-2-butanone.

33. The method as defined in claim 28 wherein the active ingredient is 1-(3,5-dichloro-6-fluoro-2-pyridinyloxy)-3,3-dimethyl-1-(1H-1,2,4-triazol-1-yl)-2-butanone.

34. The method as defined in claim 30 wherein the active ingredient is 1-(3,5,6-trifluoro-2-pyridinyloxy)-3,3-dimethyl-1-(1H-1,2,4-triazol-1-yl)-2-butanone.

35. The method as defined in claim 30 wherein the active ingredient is 1-(6-fluoro-2-pyridinyloxy)-3,3-dimethyl-1-(1H-1,2,4-triazol-1-yl)-2-butanone.

36. The method as defined in claim 28 wherein the active ingredient is 1-(5,6-dichloro-2-pyridinyloxy)-3,3-dimethyl-1-(1H-1,2,4-triazol-1-yl)-2-butanone.

* * * * *